United States Patent [19]
Bernard et al.

[11] Patent Number: 5,274,548
[45] Date of Patent: Dec. 28, 1993

[54] METHOD FOR THE AUTOMATIC ANALYSIS OF SIGNALS BY MEANS OF SEGMENTATION AND CLASSIFICATION

[75] Inventors: Marc Bernard; Michel Bouchoucha, both of Paris, France

[73] Assignee: France Telecom-Etablissement Autonome De Droit Public (Centre National D'Etudes Des Telecommunications) & Assistance Publique-Hopitaux De Paris France, Paris, France

[21] Appl. No.: 706,394

[22] Filed: May 28, 1991

[30] Foreign Application Priority Data

May 30, 1990 [FR] France .................................. 90 06728

[51] Int. Cl.$^5$ ............................................. G06F 15/42
[52] U.S. Cl. ............................ 364/413.01; 364/413.02
[58] Field of Search ............... 364/486, 487, 572, 574, 364/413.01, 413.02, 413.03, 413.05, 413.06; 128/901

[56] References Cited

U.S. PATENT DOCUMENTS

| | | | |
|---|---|---|---|
| 4,562,549 | 12/1985 | Tanaka et al. | 364/486 |
| 4,587,976 | 5/1986 | Schmid et al. | 364/413.02 |
| 4,908,771 | 3/1990 | Piot | 364/486 |
| 4,974,598 | 12/1990 | John | 364/413.06 |
| 5,003,986 | 4/1991 | Finitzo et al. | 364/413.05 |
| 5,043,927 | 8/1991 | Jackson | 364/574 |
| 5,092,343 | 3/1992 | Spitzer et al. | 364/413.05 |

OTHER PUBLICATIONS

Proceedings of Pattern Recognition, 1982, pp. 988–990, IEEE Catalogue, No. 83CH1801-0.
Proceedings of the 8th International Conference on Pattern Recognition, IEEE Catalogue No. 86CH2342-4 pp. 380-382.
IEEE Transactions on Biomedical Engineering, vol. BME-33, No. 10 pp. 972-974.
D. Castell et al., "Computer-Aided Analysis of Human Esophageal Peristalsis", Digestive Diseases and Sciences, vol. 29, No. 1, Jan. 1984 pp. 65-74.
J. Castell et al., "Computer-Analysis of Human Esophageal Peristalsis and Lower Esophageal Sphincter Pressure", Digestive Diseases and Sciences, vol. 31, No. 11, Nov. 1986 pp. 1211-1216.

*Primary Examiner*—Robert A. Weinhardt
*Attorney, Agent, or Firm*—Pearne, Gordon, McCoy & Granger

[57] ABSTRACT

A method for the automatic analysis of signals by segmentation and classification. To segment the signal, the method is carried out repeatedly by aggregating samples and merging adjacent pulses. Once segmentation has been obtained, classification is carried out. The method has particular application to the analysis of signals with a physiological origin.

5 Claims, 4 Drawing Sheets

METHOD FOR THE AUTOMATIC ANALYSIS OF SIGNALS BY MEANS OF SEGMENTATION AND CLASSIFICATION

FIELD OF THE INVENTION

The present invention concerns a method to automatically analyze signals by means of segmentation and classification.

BACKGROUND OF THE INVENTION

The invention may in particular be applied in the field of biomedicine, especially in the processing of signals having a physiological origin. The first targetted application concerns the analysis of esophageal contraction signals, but the method may equally be applied to any noised pulse signal.

The accompanying FIG. 1 shows the shape of peristaltic waves originating from signals to be processed (in the application in question).

At (a), the figure shows the act of swallowing which triggers a pressure variation (P) firstly giving rise to a proximity wave (b) which moves and deforms (c, d).

An analysis of the esophageal contraction signals results in measuring various quantities, such as the amplitude A of the peak, the period D of the pulse, the maximum slopes of the rise and fall fronts (dP/dt)M, the area under the curve S, etc.

Statistical analyses are also undertaken so as to obtain the number and percentages of the various types of pulses appearing in all the signals measured (peristaltic, tertiary, polyphasic waves, etc).

All these results are important factors for a clinician.

The physical entity, quality or property to be treated (pressure, PH, etc) is measured by various probes (esophageal, intestinal, PHmetric) or sensors. The signals representative of this entity are then amplified and recorded. With the arrival of the computer, the carrying out of measurements is no longer effected manually but by data processing methods. In order to do this, the signal is sampled and stored in a computer provided with display (screen) or printing means.

This technique is described in the document entitled "Computer-Aided Analysis of Human Esophageal Peristalsis-(I) Technical Description and Comparison with Manual Analysis" by Donald O. CASTELL and al and published in the journal "Digestive Diseases and Sciences", vol. 29, No 1, January 1984, pp. 65–72 and in "Computer Analysis of Human Esophageal Peristalsis and Lower Esophageal Sphincter Pressure. (II) An Interactive System for On-Line Data Collection and Analysis" by June A. CASTELL and al and published in "Digestive Diseases and Sciences", vol. 31, No. 11, November 1986, pp. 1211–1216.

In such processing methods, each pulse is defined, not by all the points constituting it, but by several parameters, such as the start and end samples and the peak (or top) sample, all samples defined by their amplitude and time of appearance.

The two articles referred to on the whole demonstrate that resorting to using a computer proves to be soundly-based and reliable to the extent that the results obtained satisfactorily match results obtained manually.

Although constituting a certain element of progress, this technique does nevertheless have a certain number of drawbacks, especially as regards that it is semiautomatic and requires the intervention of a practitioner during analysis so as to initialize the method (mainly at the start of analysis). The fundamentally non-stationary nature of the phenomena studied complicates the task involved.

SUMMARY OF THE INVENTION

The object of the invention is to overcome this drawback by proposing an entirely automatic analysis method relieving the doctor from having to carry out the fastidious marking of significant signals. The method of the invention is not merely automatic, but a priori requires scarcely any information concerning the signal, which renders the method particularly reliable for medical applications.

The method of the invention is principally divided into two portions: segmentation and classification:

for segmentation, the pulses linked to the phenomenon studied are detected with the aid of a pulse growth method using merging operators implementing criteria linked to the shape of the signal;

for classification, all the pulses obtained are classified by implementing data analysis methods enabling the significant portions to be separated from the noise.

In the first part of the method relating to the detection of pulses by means of segmentation, this detection is effected by looping : a first segmentation is carried out by fixing arbitrary thresholds for the pulse merge operations. Then an excess segmentation of the signal is obtained. On the basis of the result obtained, new thresholds are fixed and the segmentation is repeated; this is continued until the number of mergings no longer increases. The signal finally obtained is then subjected to the second part of the method, namely classification.

BRIEF DESCRIPTION OF THE DRAWINGS

The characteristics and advantages of the invention shall appear more readily from a reading of the following description relating to embodiment examples given by way explanation and being non-restrictive with reference to the accompanying drawings on which.

DETAILED DESCRIPTION OF THE PREFERRED EMBODIMENTS

Figure 2:
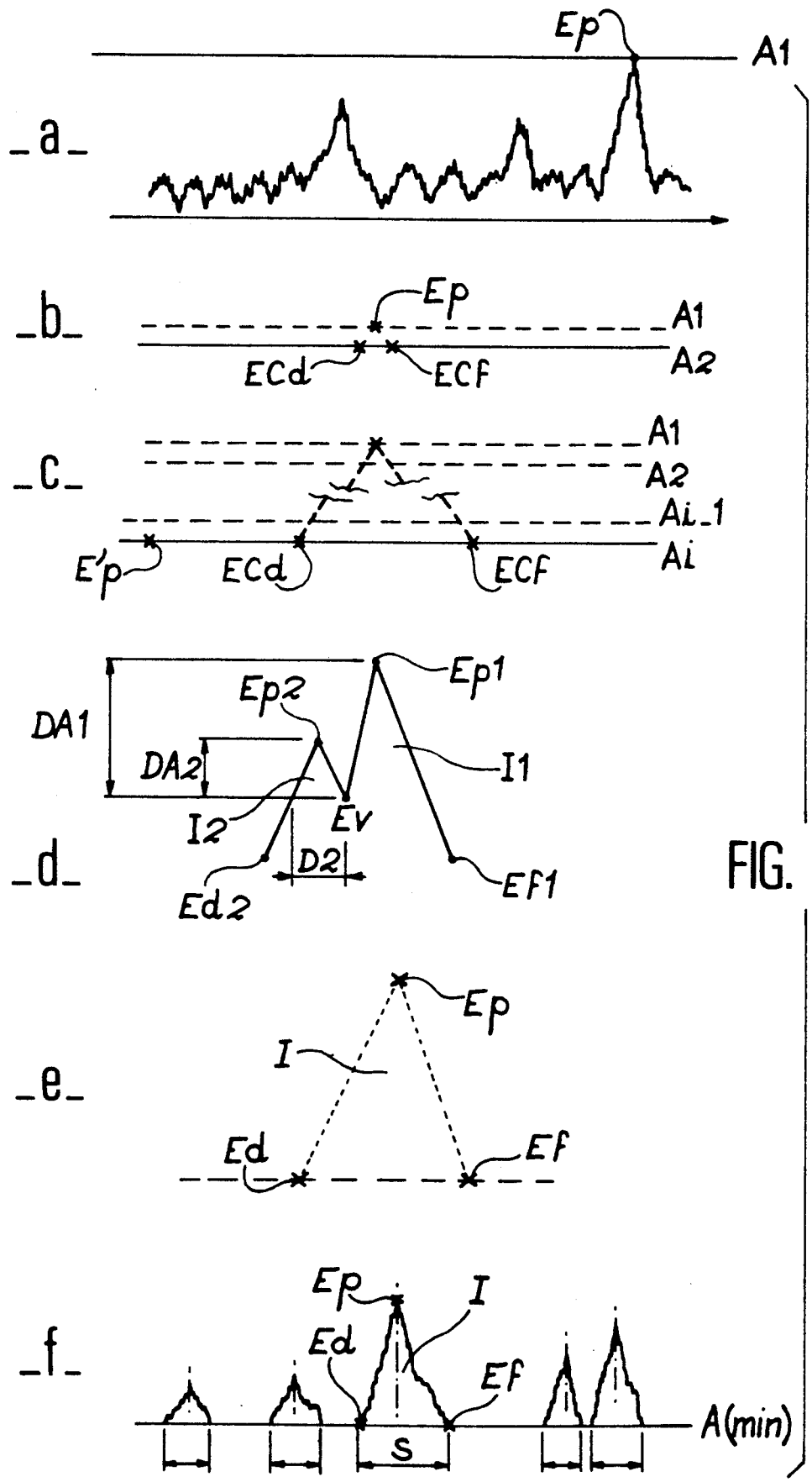
FIG. 2 shows various stages in the segmentation operation.

The first phase of the method of the invention, intended to segment the signal into sections, each corresponding to one pulse, is illustrated by FIG. 2 (lines (a) to (e)).

a) Line (a) of FIG. 2 shows one portion of a recorded pulse signal. First of all, an analysis amplitude is fixed having a value A1 equal to the maximum amplitude of the stored samples. The corresponding sample Ep is taken as being the sole sample marking the start, peak and end of a first pulse to be established.

b) Then the analysis amplitude is lowered by a specific quantity and the stored samples having the new lowered amplitude A2, line (b), are looked for;

c) For each sample found (actually, there are only two, namely ECd and ECf), a check is made to determine whether or not the sample is connected to the sample Ep already found in the preceding operation a), and:

c1) if the sample is connected, it is taken as being a new start sample ECd or new end sample ECf of the first pulse being constituted, c2) if the sample is not connected, it is taken as being a new start, peak or end sample of a new pulse to be established.

d) the operations b) and c) are repeated by progressively lowering the analysis amplitude A2, . . . , Ai-1, Ai (line c). The connected pulse start and end samples are thus gradually aggregated to the pulses being constituted. But new samples appear, such as E'p on line c); these are taken as being peaks of new pulses to be constituted. Thus, pulses can gradually be seen.

e) On each repeat of the operation d), two pulses I1 and I2 being constituted are merged into a single one (cf line d) if: e1) they have in common a sample Ev, this sample defining a valley between the two peaks Ep1 and Ep2, e2) having calculated for each pulse I1, I2 the difference between the amplitude of the peak sample Ep1, Ep2 and the amplitude of the common valley sample Ev, the ratio of these differences is greater than a first threshold T1, e3) the period of the pulse with the smallest amplitude difference between the peak Ep2 and the valley Ev (in the case shown on line d, it is the pulse I2) which is lower than a second threshold T2, e4) the two peak/valley amplitude differences are lower than one third threshold T3.

The merging of two pulses I1, I2 into a single pulse I (cf line e) consists of taking firstly for the start sample of the single pulse the start sample Ed of the first pulse I2, secondly for the end sample the end pulse Ef of the second pulse I1, and finally for a peak sample the peak sample Ep of the highest of the two pulses I1.

In this merging operation, the three thresholds T1, T2, T3 have, in this first phase (A), three arbitrary values.

f) Thus, the analysis amplitude is lowered until reaching a minimum predetermined value A(min) (line f), which then leaves on the final repeat corresponding to this minimum value, a series of segments S each defining a pulse I with a peak sample Ep, a start sample Ed and an end sample Ef.

Having obtained this first segmentation from three thresholds selected arbitrarily, segmentation shall be refined by modifying these thresholds. Three new thresholds shall be defined on the basis of the results obtained following the first segmentation. In order to do this, a statistical analysis is made of the pulses obtained (line f of FIG. 2) so as to draw up three histograms respectively relating to the peak/valley differences, the periods and the amplitudes of the pulses obtained.

Figure 3:
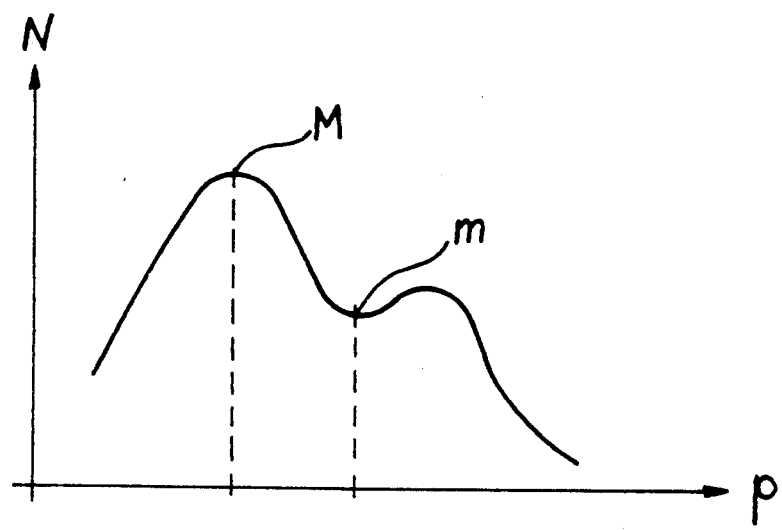
FIG. 3 shows the form of a histogram obtained after segmentation.

These histograms have the appearance of the curve of FIG. 3 which represents the number N of pulses having a certain value for the parameter p. A first maximum M corresponds to the noise pulses. It is followed by a minimum m which gives the value of the new threshold to be taken for the parameter in question (peak/valley difference, period, amplitude).

Then the operations d) to f) of the first phase are repeated with the new defined thresholds T'1, T'2 and T'3, which make it possible to resegment the signal by remerging new pulses.

After remerging the new pulses and again determining new thresholds, operations d) to f) of the first phase are repeated and so on until the processing no longer makes it possible to carry out new mergers of pulses and no longer reduces the number of pulses obtained. The signal is then definitively segmented and the series of pulses obtained is the one on which analysis may be conducted.

This segmentation operation defines a set of pulses, each characterized by their start, end and peak. But only one sub-unit of these pulses has any significance, that is the one that corresponds to the esophagial contraction signals. The other pulses correspond to the noise due to breathing, heart beats and the coughing of the patient. Thus, it is necessary to continue analysis of the signal by means of a classification making it possible to separate the significant pulses from the noise.

Preferably, a method known as the dynamic storm clouds method, is used. In this method, each pulse is quantitatively defined by parameters, such as:

the difference between the amplitude of the peak and the amplitude of the lowest extremity, the width of the pulse, the average amplitude of the pulse the width of the average amplitude pulse, the amplitude variance, the average of the slopes of the pulse rise and fall fronts, the average of the differences between the amplitude of a peak and the amplitudes of two adjacent peaks.

This represents all the pulses within a space with as many dimensions as the parameters selected, which results in a cloud of points in this space, each point corresponding to one pulse.

In the case where the seven preceding parameters are retained, a cloud of points is obtained inside a space with seven dimensions.

The cloud of points is preferably divided into two classes, the first corresponding to the significant rather short strong amplitude pulses and the second corresponding to rather weak low amplitude pulses.

According to another variant, the cloud of points obtained is divided into three classes, the first corresponding to high amplitude pulses, the second corresponding to long-period pulses, the third corresponding to the intermediate pulses, the third one then being divided into two sub-classes.

So as to adapt the relative weight of each parameter to the specific characteristics of each recording, it is again preferable to carry out a principal component analysis making it possible to analyze the cloud of points along its main axes. This processing makes it possible to more clearly separate the various classes encountered.

Figure 4:
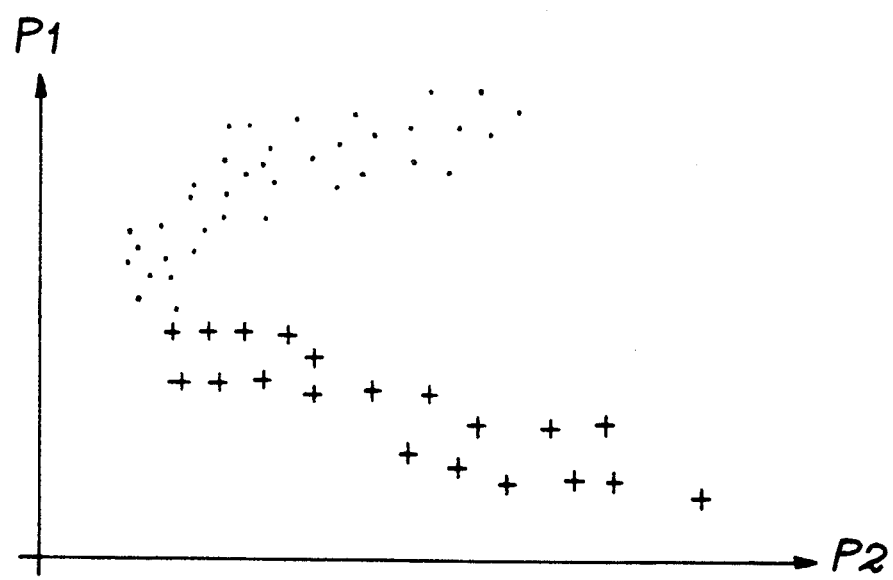
FIG. 4 diagrammatically shows a finally obtained example of a cloud of points.

FIG. 4 diagrammatically illustrates the aspect of the cloud of points displayed on a screen of a computer following the processing described immediately above. The cloud corresponds to the distribution of pulses according to two parameters P1, P2. The crosses are supposed to represent the non-significant pulses and the points of the significant pulses.

Figure 5:
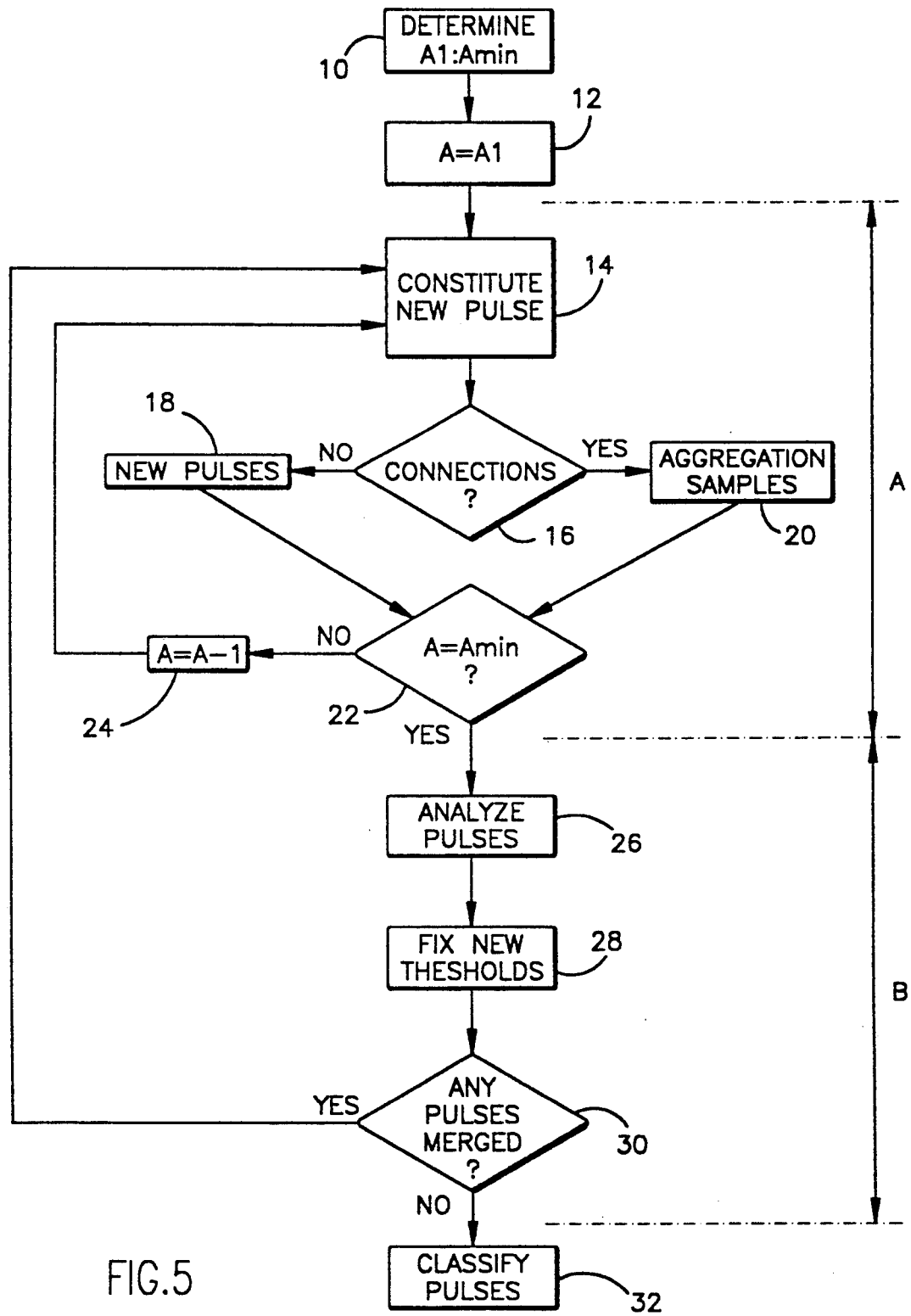
FIG. 5 is a general flow chart of the method of the invention.

FIG. 5 shows the general flow chart of the method described above. The significance of the blocks shown is as follows:

10: to determine the maximum amplitude (A1) and the minimum amplitude (Amin),

12: to give the value of the maximum to the analysis amplitude A,

Phase A

14: pulse growth operation,
16: are there any connections?
18: if there are no connections, formation of a new pulse,
20: if a connection exists, aggregation of the new sample to the currently growing pulse,
22: is the analysis amplitude equal to the minimum amplitude.
24: if the answer to question 22 is negative, make $A = A - 1$, that is reduce the analysis amplitude,

Phase B

26: if the answer to question 22 is affirmative, carry out the statistical analysis of the pulses obtained,
28: fix new thresholds,
30: have the pulses been merged since the last repeat? If so, repeat the pulse merging operations with the new thresholds ; if not, the analysis is ended,
32: classification of pulses.

Figure 1:
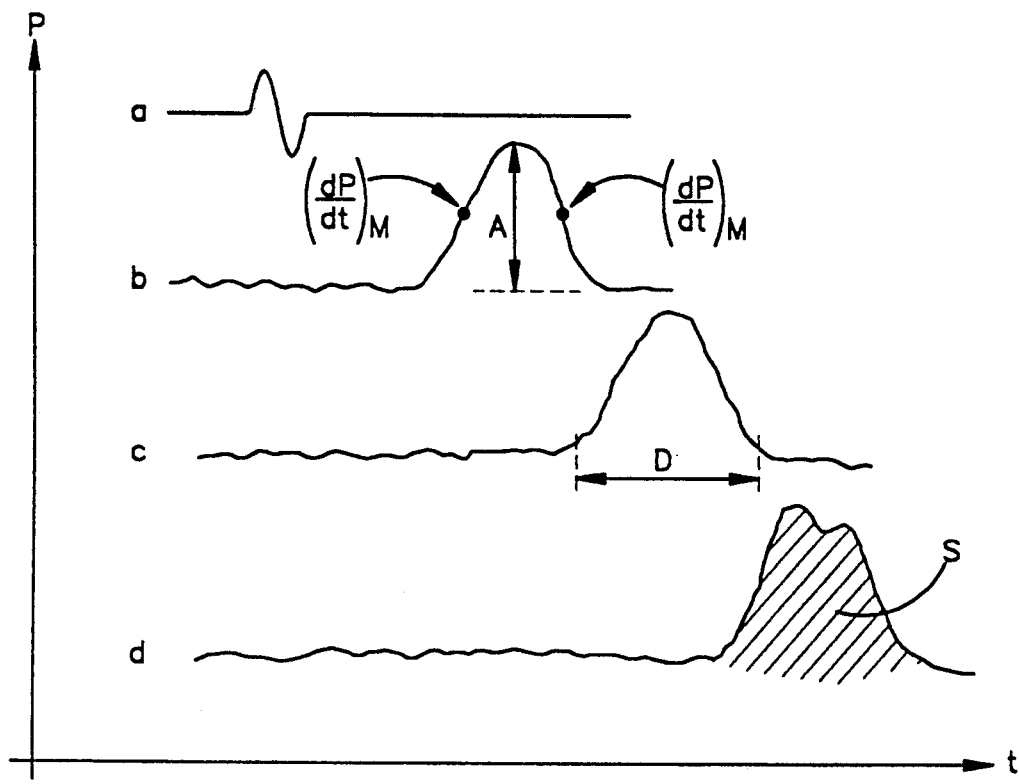
FIG. 1, already described, shows the appearance of the signals to be processed.
Figure 6:
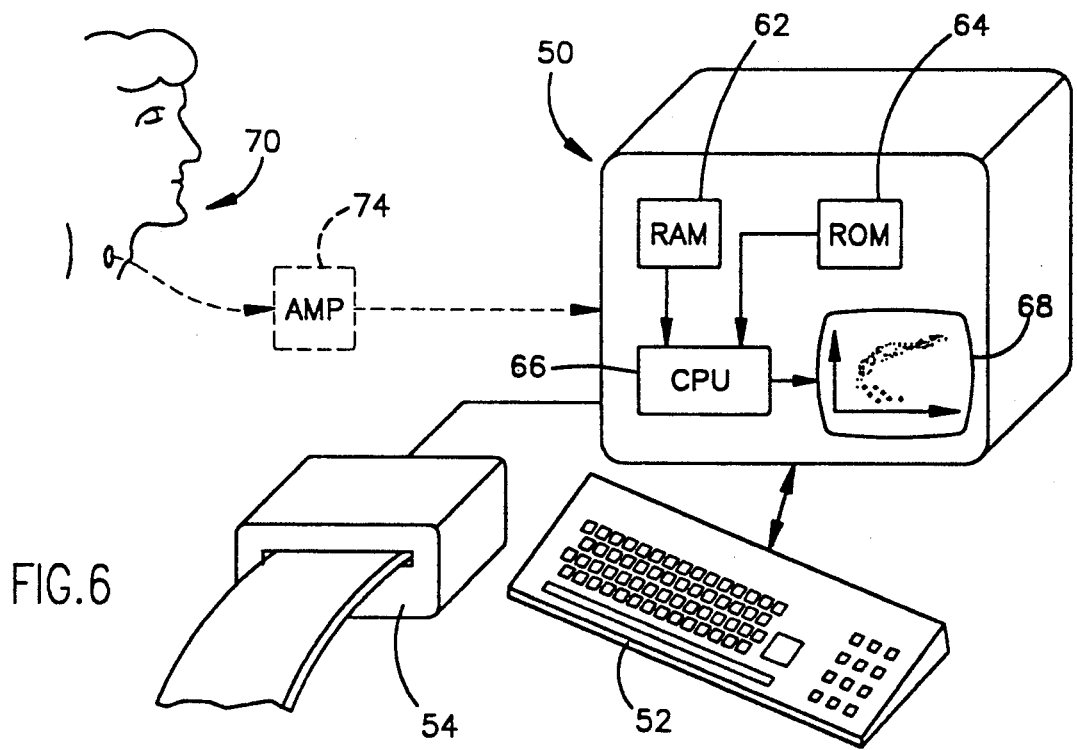
FIG. 6 shows an installation able to implement the method of the invention.

Finally, FIG. 6 diagrammatically shows a device able to implement the method described above. This device includes a computer 50 (which may be a PC type computer), a keyboard 52 and a printer 54. The computer includes a memory 62 containing the data to be processed (in the form of a floppy disk, for example), a ROM type memory 64 containing the processing program, a central processing unit 66 and a screen 68.

Again, FIG. 6 shows a patient 70 on whose esophagus a probe 72 has been placed able to measure the pressure. An amplifier 74 makes it possible to deliver an electric signal which is next sampled and then digitally-converted and stored in the memory 62 of the computer.

Of course, the method described above may be carried out differently, that is by firstly recording the signal on a suitable medium (such as a floppy disk) independently of the computer and then insert at the desired moment this medium into a computer so as to process the signal.

What is claimed is:

1. Method for automatic analysis of an original pulse signal, wherein a physical property is measured and the measurement is converted into digital data which is stored and subsequently processed so as to extract from it significant pulses and obtain selected statistical characteristics of the physical property measured, the process for extracting the significant original pulses including the following operations:

A) in a first phase: segments are defined in the signal, each of these segments corresponding to one original pulse having one start sample marking one extremity of the segment, one peak sample marking the top portion of the original pulse, and one end sample marking the other extremity of the segment, this first plane, known as the segmentation phase, including the following operations:
  a) an analysis amplitude with a specific value is fixed equal to the maximum amplitude of the samples, the corresponding sample being taken as a start, peak and end samples of a first pulse to be constituted,
  b) the analysis amplitude is lowered by a specific quantity and samples having this new lowered amplitude are sought,
  c) for each such sample found, an investigation is made to discover whether the found sample is connected to the sample found in the preceding operation a) and:
  c1) if the sample is connected, it is taken as being a new start sample or end sample of the pulse being constituted,
  c2) if the sample is not connected, it is taken as being a new start, peak and end sample of a new pulse to be constituted,
  d) the operations b) and c) are repeated by progressively lowering the analysis amplitude, which gradually aggregates connected pulse start and end samples to those pulses being constituted and causes new samples to appear which are taken as being peaks of new pulses to be constituted,
  e) on each repeat of the operation d), two pulses being constituted are merged into a single one if:
  e1) they possess in common a sample defining a valley between the two peaks of the two pulses,
  e2) having calculated for each pulse a difference between the amplitude of the peak sample and the amplitude on the common valley sample, a ratio of these differences is greater than a first threshold,
  e3) the period of the pulse having the smaller peak/valley amplitude difference is smaller than a second threshold, and
  e4) the two peak/valley amplitude differences are lower than a third threshold, the merging of two pulses into one single pulse consisting of taking, for a start sample of the single pulse, the start sample of the first pulse, for an end sample of the single pulse, the end sample of the second pulse, and for a peak sample of the single pulse, the peak sample of the highest of the two pulses, the three thresholds having in this first phase three arbitrary values,
  f) the analysis amplitude is lowered until it reaches a minimum predetermined value so as to define on a final repeat of step d) corresponding to this minimum value, a series of segments each defining one pulse with a peak amplitude, a period and a peak/valley difference, B) in a second phase;
  g) a statistical analysis is carried out of the pulses obtained after the first segmentation phase and three histograms are determined relating respectively to the peak/valley differences, the periods and the amplitudes of the pulses obtained,
  h) on the basis of the three histograms obtained, three new thresholds are defined respectively for the ratio of the peak/valley differences, the period and for the peak/valley differences,
  i) the operations d) to f) of the first phase are repeated with these new thresholds to resegment the signal by redefining and remerging new pulses, and
  j) with the new pulses obtained after the operation i), the operations d) to h) of the first phase are repeated until the operations no longer allows any new mergings to be carried out and no longer reduces the number of pulses obtained, which leaves a definitively segmented signal with a definitive set of pulses on which analysis is then carried out.

2. Method according to claim 1, wherein it includes, following the second phase, a pulse classification operation in which:
  a) each pulse is quantitatively defined by selected parameters, and b) all the pulses obtained are represented inside a space with as many dimensions as the number of selected parameters, which results in a cloud of points inside this space, each point corresponding to one pulse, the cloud obtained being analyzed.

3. Method according to claim 2, wherein the cloud of points obtained is divided into two classes for further analysis, the first class corresponding to rather short high amplitude significant pulses and the second class corresponding to rather long low amplitude pulses.

4. Method according to claim 2, wherein first the cloud of points obtained is divided into three classes for further analysis, the first class corresponding to high amplitude pulses, the second class to extremely long-duration pulses, the third class corresponding to intermediate pulses, the third class then being divided into two sub-classes.

5. Method according to claim 2, wherein a principal component analysis is conducted on the obtained cloud of points.

* * * * *

UNITED STATES PATENT AND TRADEMARK OFFICE
CERTIFICATE OF CORRECTION

PATENT NO. : 5,274,548

DATED : December 28, 1993

INVENTOR(S) : Marc Bernard and Michel Bouchoucha

It is certified that error appears in the above-identified patent and that said Letters Patent is hereby corrected as shown below:

```
Column 3, line 32, delete "one" and insert --a--.

Column 3, line 62, delete "m" and insert --m--.

Column 5, Claim 1, line 62, delete "samples" and insert --
     sample--.

Column 6, Claim 1, line 21, delete "on" and insert --of--.

Column 6, Claim 1, line 58, delete "operations" and insert
     --operation--.
```

Signed and Sealed this

Twenty-sixth Day of July, 1994

Attest:

BRUCE LEHMAN

*Attesting Officer*  *Commissioner of Patents and Trademarks*